United States Patent
Mueller

[11] Patent Number: 5,871,495
[45] Date of Patent: Feb. 16, 1999

[54] METHOD AND APPARATUS FOR MECHANICAL TRANSMYOCARDIAL REVASCULARIZATION OF THE HEART

[75] Inventor: Richard L. Mueller, Sunnyvale, Calif.

[73] Assignee: Eclipse Surgical Technologies, Inc., Sunnyvale, Calif.

[21] Appl. No.: 713,531

[22] Filed: Sep. 13, 1996

[51] Int. Cl.⁶ ................................................ A61B 17/34
[52] U.S. Cl. ............................................. 606/185; 606/167
[58] Field of Search ............................ 128/88; 606/1, 606/108, 167, 170, 171, 180, 181, 184, 185; 604/272

[56] References Cited

U.S. PATENT DOCUMENTS

| | | | |
|---|---|---|---|
| 4,576,162 | 3/1986 | McCorkle | 606/180 |
| 4,658,817 | 4/1987 | Hardy | 606/7 |
| 5,358,472 | 10/1994 | Vance et al. | 606/22 |
| 5,380,316 | 1/1995 | Aita et al. | 606/7 |
| 5,403,311 | 4/1995 | Abele et al. | 606/50 |
| 5,591,159 | 1/1997 | Taheri . | |

FOREIGN PATENT DOCUMENTS

| | | |
|---|---|---|
| 0 807 412 A1 | 11/1997 | European Pat. Off. . |
| WO 96/35469 | 11/1996 | WIPO . |

*Primary Examiner*—Glenn K. Dawson
*Attorney, Agent, or Firm*—Janet Kaiser Castaneda

[57] ABSTRACT

An apparatus for creating revascularization channels in tissue, such as the myocardium of the heart, mechanically cuts the channels using a hand piece with easily removable cutting tip assemblies having angled, sharpened edges to allow rapid tip replacement. The cutting tip assembly has an inner needle within an outer hollow needle with each needle attached to the hand piece for independent rotation and axial movement. The inner needle may be hollow, or formed with a pointed tip, and may rotate counter to the outer needle to enhance gripping and storage of the tissue excised by the outer needle. The hand piece may attach a cylindrical magazine of cutting tip assemblies or one cutting tip assembly. The cutting tip assembly may be heated to provide thermal damage to the heart muscle during the creation of the channel, providing some of the advantages of the laser method of TMR.

9 Claims, 5 Drawing Sheets

METHOD AND APPARATUS FOR MECHANICAL TRANSMYOCARDIAL REVASCULARIZATION OF THE HEART

FIELD OF THE INVENTION

This invention relates to the field of surgical interventions for correction of coronary disease, and more particularly to the methods and devices for transmyocardial revascularization of the heart.

BACKGROUND OF THE INVENTION

Heart disease is a significant health problem which has been the subject of substantial medical study. Bypass surgery has become commonplace; yet such surgery may be unavailable to many patients, either because of the nature of the occlusions or the physical condition of the patient.

One promising alternative technique for treating such cases is known as trans-myocardial revascularization (TMR). Although this technique was considered as early as the work of Dr. C. Beck "the Development of a New Blood Supply to the Heart By Operation", *Annals of Surgery*, Vol. 102, No. 5 (11/35) pp. 801–813, the method was not extensively studied until the work of Dr. M. Mirhoseini and M. Cayton, an example of which is found in "Lasers in Cardiothoracic Surgery" in *Lasers in General Surgery* (Williams and Williams; 1989) pp. 216–223.

An early device to perform TMR is described in Aita et al., U.S. Pat. No. 5,380,316, issued Jan. 10, 1995. In the procedure described in that patent, a number of channels are formed through the myocardium between the ventricle and the exterior of the heart through the epicardium and myocardium by means of a laser apparatus. These channels were approximately 1.5 mm–2.0 mm in diameter and approximately 1 to 3 cm deep. Clinical tests have demonstrated that such channels facilitate revascularization of the heart muscle and recovery of heart function.

Unfortunately, this technique has some attendant difficulties. The laser equipment for performing such procedures is large and expensive and may be unavailable to smaller and more remote medical facilities. Some patients may therefore find it difficult to gain access to a properly equipped medical facility when treatment is needed.

One alternative to the use of lasers would be to use a mechanical cutter to produce the channels. Unfortunately, as noted in the Aita et al. patent, prior art methods of mechanical piercing and cutting of the heart wall produce tearing of the tissue. Such tearing leads to fibrosis, which combined with the problems of maintaining clear, clean channels, seriously diminishes the effectiveness of the TMR treatment produced by such methods. Hence, such prior art mechanical piercing does not adequately facilitate rapid and clean healing of channels.

Another alternative approach, melting of the myocardium by hot probes, has proven unsatisfactory, partly because there is no mechanism for removal of melted material from the channel.

It would therefore be desirable to produce clear, clean channels using relatively inexpensive and easily transportable systems, which may be deployed in remote locations.

SUMMARY OF THE INVENTION WITH OBJECTS

Broadly, an advantage of the present invention is to provide an apparatus and method for producing viable channels suitable for TMR without the use of lasers.

More specifically, an advantage of the present invention is to provide an apparatus and method for mechanically performing TMR without excessive tearing or other complications which cause blockage of the created channels.

It is a further advantage of the present invention to provide an apparatus and method for mechanically performing TMR without a requirement for large, expensive equipment.

Yet another advantage of the present invention is to provide a hollow cutting device, which may or may not be heated, for mechanically cutting and removing myocardial tissue to create channels in the myocardium.

Still one more advantage of the present invention is to provide a hand held tool for deploying cutting devices for non-laser TMR procedures.

The present invention comprises a method and apparatus for mechanically performing transmyocardial revascularization (TMR). Although the invention may be implemented in a variety of embodiments, several of which are illustrated herein, all require an apparatus with a special cutting tip assembly, preferably an easily removable cutting tip assembly which would allow rapid replacement to permit several channels to be created in a relatively short period of time. This cutting tip assembly has means for supporting the assembly in location on the heart wall while in operation. In several of the embodiments shown herein, the support means may include suction to assist in clean, complete removal of the material excised from the heart wall by the cutting tip assembly during formation of channels. In all embodiments there also is a mechanical means present to remove that material which is to be excised to form the channel. Preferably, the cutting tip assembly is removably mounted to a hand piece with an actuator to deploy, rotate, and remove the cutting tip assembly. The hand tool may accommodate one or more cutting tip assemblies.

The cutting tip assembly optionally may be heated to provide thermal damage to the heart muscle during the creation of the channel, providing some of the advantage of the laser method of TMR. Such heating may be provided by placing the cutting tip assembly in a specially designed heater base which permits rapid connection of the assembly to the remainder of the apparatus while the cutting tip assembly is still in the heater. In this way the cutting tip assembly may be maintained at optimal temperature until the apparatus is ready to be deployed.

These and other objects, advantages and features of the present invention will be apparent to those skilled in the art from the following detailed description and the accompanying drawings.

BRIEF DESCRIPTION OF THE DRAWINGS

FIG. 3A illustrates a drill style inner needle; FIG. 3B illustrates a screw style inner needle; and FIG. 3C illustrates an inner needle defining a side cut and a piercing tip.

DETAILED DESCRIPTION OF THE PRESENT INVENTION

While a variety of embodiments of the present invention are disclosed herein, one exemplary presently preferred embodiment is illustrated in FIGS. 1A through 1D. FIGS. 1A through 1D each represent a different stage in the process of creating a channel 18 in the myocardium 10, which has an outer wall (epicardium) 12 and an inner wall (endocardium) 14.

Figure 1A:
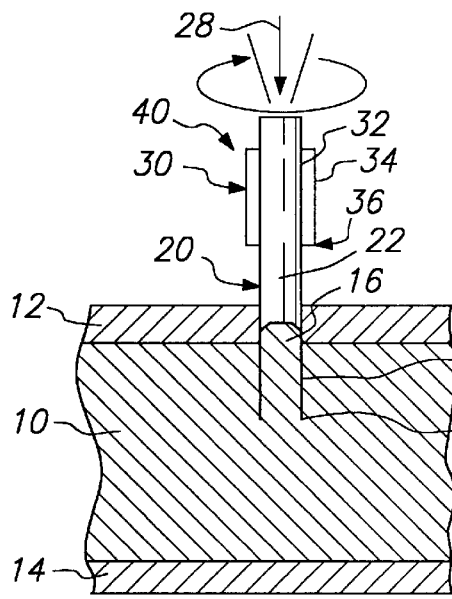
FIGS. 1A–1E illustrate a presently preferred method and apparatus according to the present invention, utilizing a cutting tip assembly comprising two concentric rotatable needles.

FIG. 1A illustrates that the apparatus of this embodiment of the present invention has a cutting tip assembly 40 with an inner cylindrical needle 20, which has a tubular hollow internal bore 22 within its body 24. Because inner needle 20 is cylindrical, it has a longitudinal axis 28. Inner needle 20 has a sharpened edge 26, which may be made sharp through use of a variety of geometries (e.g., beveled inward, beveled outward). A presently preferred cutting edge defines an angle less than 45 degrees, and preferably less than 30 degrees, from the longitudinal axis 28. The cutting edge is sharpened using conventional techniques used in, for instance, the production of razor blades. Use of a newly sharpened cutting edge for each channel is recommended to reduce drilling trauma, tissue wrapping forces, and create cleanly excised channels.

Figure 1B:
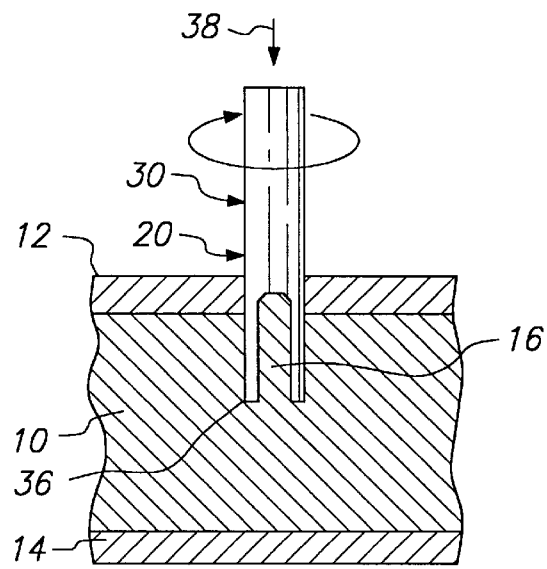
Figure 1C:
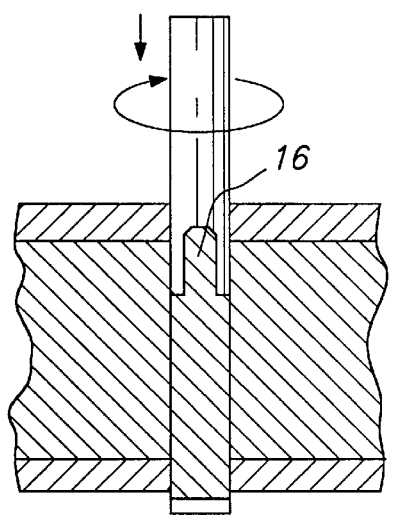
Figure 1D:
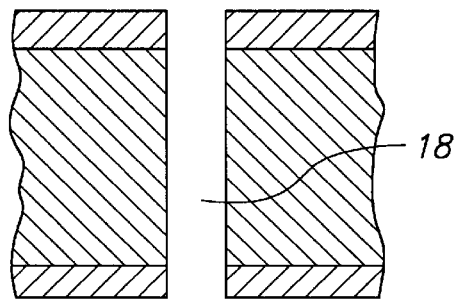
Figure 1E:
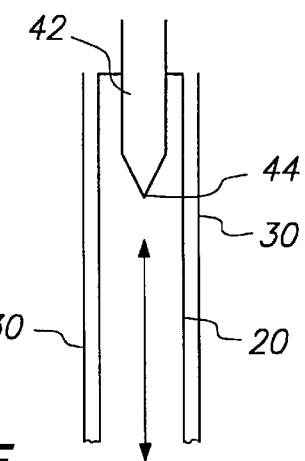

As shown in FIG. 1E, the inner needle 20 also may have a sharpened retractable piercing tool 42 with a sharped point 44 for making a small, initial incision through the epicardium, as better described below. The piercing tool 42 moves upwardly and downwardly as shown by the directional arrow in FIG. 1E with such movement being controlled conventionally using manual or automatic control methods and apparatus.

FIGS. 1A–1E further illustrate that the cutting tip assembly 40 has an outer cylindrical needle 30, which has a tubular hollow internal bore 32 within its body 34. Again, because outer needle 30 is cylindrical, it has a longitudinal axis 38. Outer needle 30 has a sharpened edge 36, which also is made sharp through use of a variety of geometries (e.g., beveled inward, beveled outward) using the sharpening techniques discussed above, and may define an angled cutting edge as described in connection with inner needle 20.

Outer needle 30 is disposed relative to inner needle 20 roughly surrounding inner needle 20 (which may also be viewed as inner needle 20 being disposed within the internal bore 32 of outer needle 30). The longitudinal axis 28 of inner needle 20 and longitudinal axis 38 of outer needle 30 need to be substantially coincident; such an arrangement of needles should allow relative longitudinal translation between inner needle 20 and outer needle 30, as well as differential rotation of the two needles, as shall be described below.

Figure 3A:
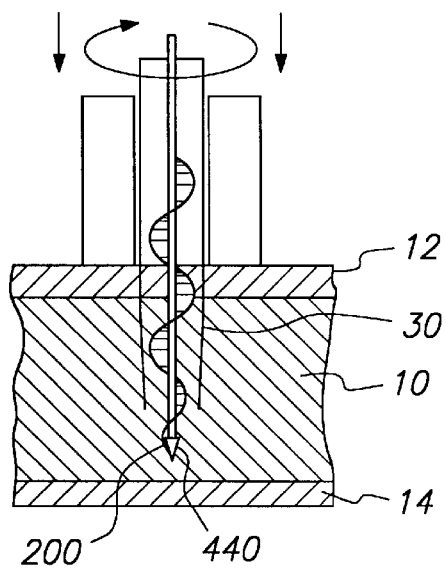
FIGS. 3A–3C illustrate additional aspects of inner needles of cutting tip assemblies comprising two needles.
Figure 3C:
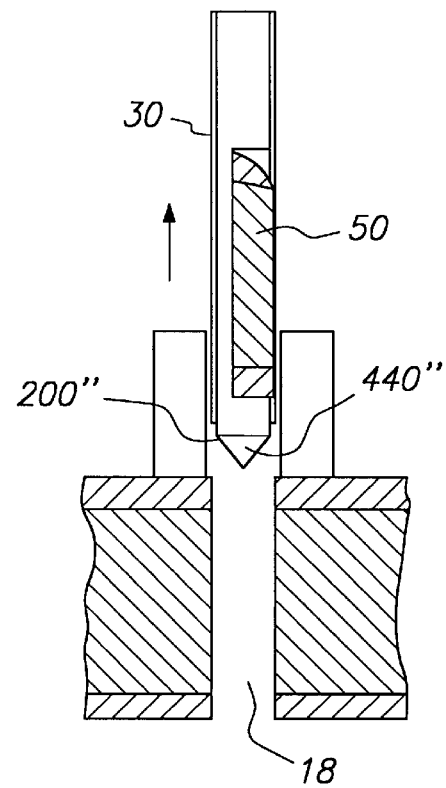
Figure 3B:
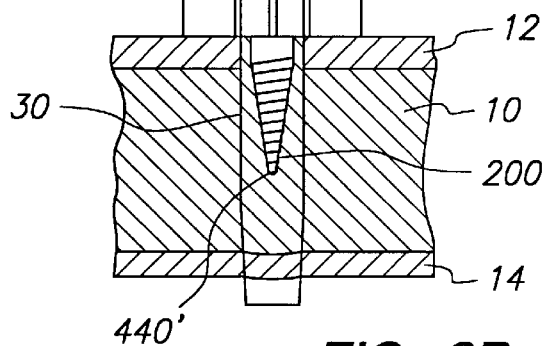

Alternative aspects of the inner needle are shown in FIGS. 3A and 3B. In FIG. 3A, the inner needle is formed as a sharped, spiraled drill 200 which may be rotated downwardly with the outer needle 134. The drill needle configuration 200 defines a sharpened piercing tip 440 serving the same purpose as point 44 in FIG. 1E and further functions to pull excised tissue upwardly into the hollow outer needle 30. The drill needle 200 may or may not be rotated at the same speed and same time as the outer needle 30. In FIG. 3B, the inner needle 200' is formed as a screw mechanism 200' which may be rotated to advance into myocardial tissue 10. The screw mechanism 200' may be held stationary within the myocardium 10 as the outer needle 30 is rotated and moved downward to cut a channel through the myocardium 10 and, preferably, through the endocardium 14 the screw mechanism 200' also includes a pointed piercing tip 440'. Removal of the screw mechanism 200' (or the drill needle 200) and the outer needle 30 causes removal of the excised myocardial tissue which is held by the screw or drill mechanism 200, 200' within the hollow outer needle 30. FIG. 3C illustrates an additional aspect of an inner needle 200'' which defines a side cut aperture 50 for holding excised tissue and a sharpened piercing tip 440''.

Any of the inner and outer needle arrangements shown in FIGS. 1A–1E and 3A–3D enable initial piercing of the epicardium utilizing the point 44 in conjunction with FIGS. 1A–1E or the piercing tips (440, 440', 440'') of the inner needle in conjunction with FIGS. 3A–3C to create a small hole for entry into the myocardium. Alternatively, the smaller bore inner needle 20 may be used to create the initial opening. The creation of a small entry point is preferred to decrease bleeding at the epicardial surface and reduce any tendency for the formation of adhesions between the epicardium and the pericardial sac. The inner needle (20, 200, 200', or 200'') is advanced into the myocardium and stabilizes the entire cutting tip assembly by embedding the inner needle into myocardium. The embedded inner needle serves as an anchor to secure the assembly to the beating heart while the outer needle is rotated and advanced. The inner needles described above also hold the excised tissue in place, prior to retracting that tissue, and ensure that excised tissue is evenly distributed within the internal bore of the outer needle as the outer needle is advanced and retracted.

Another preferred embodiment of the present invention having a cutting tip assembly 400 with a single needle 402 is illustrated in FIGS. 2A through 2D. Again, FIGS. 2A through 2D each represent a different stage in the process of creating a channel 18 in the myocardium, or heart wall 10, which has an outer wall 12 and an inner wall 14.

A support means 100 with a tubular hollow internal bore 102 within its body 104 is placed against outer heart wall 12. The support means 100 may be a generally disk shaped block with a frictional contact surface, preferably with vacuum apparatus 106 to assist in removal of excised tissue and to provide a counter force to the cutting tip assembly 400. Because the internal bore 102 of the support means is cylindrical, it has a longitudinal axis 108. Alternatively, the support means may be a wall surrounding an aperture for inserting the cutting tip assembly into a hand piece, to be described below.

The tapered needle single needle 402 has a hollow internal bore 404 within its body 406. Again, because tapered needle 402 is cylindrical, it has a longitudinal axis 408. Tapered needle 402 has an edge 406, which may be made sharpened and angled as described in connection with the FIG. 1A–1D and 3A–3D embodiments above.

Tapered needle 402 is disposed relative to support means 100 by being disposed within the internal bore 102 of support means 100. The longitudinal axis 108 of internal bore 102 and longitudinal axis 408 of tapered needle 400 need to be substantially coincident; such an arrangement of needles should allow relative longitudinal translation between tapered needle 402 and internal bore 102, as well as rotation of tapered needle 402. A piercing tool, such as tool 42 shown in FIGS. 1A–1E also may be used within the bore of tapered needle 402.

Figure 5:
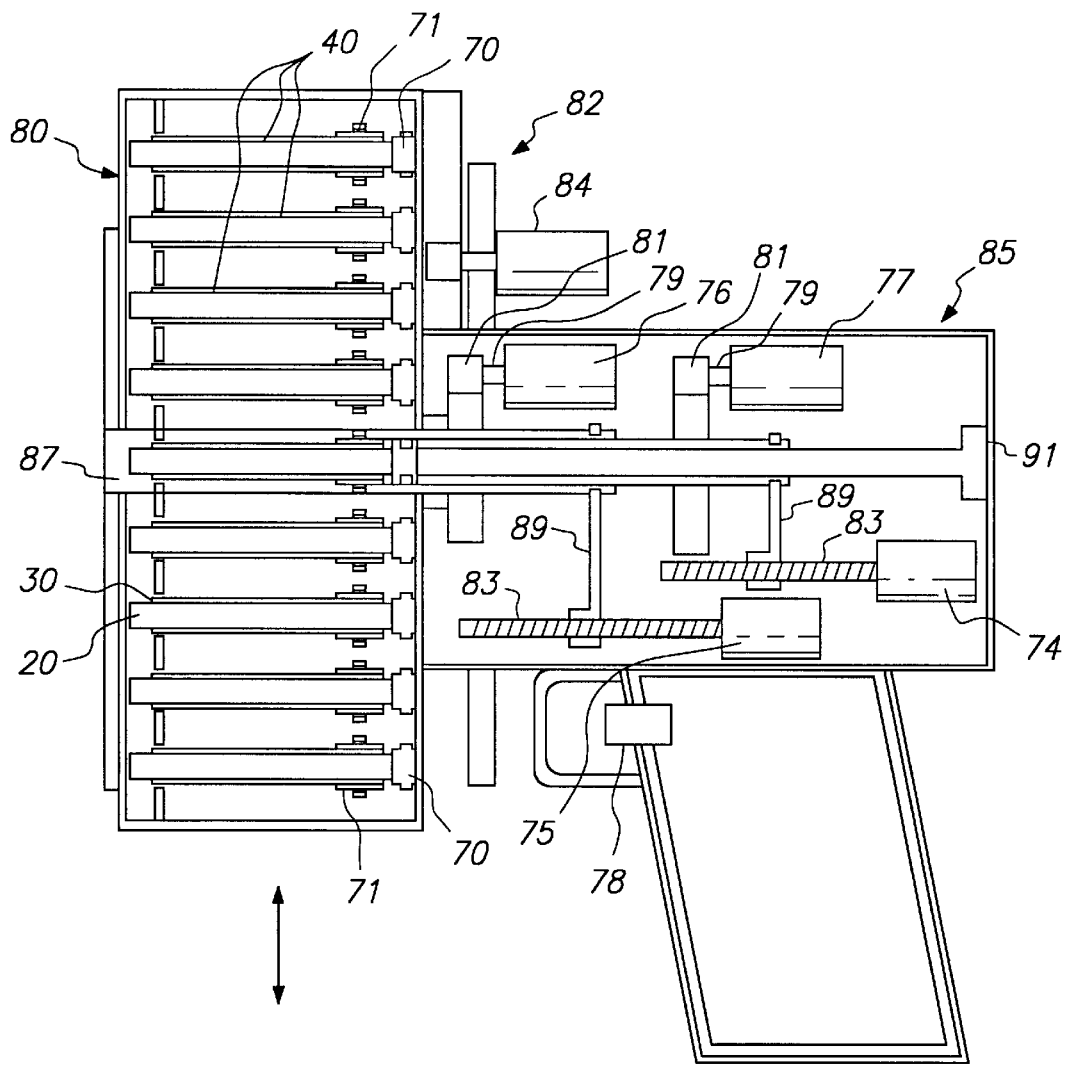
FIG. 5 is a side view of a preferred hand piece having a cylindrical magazine, shown linearly for purposes of illustration only, holding multiple cutting tip assemblies.
Figure 6:
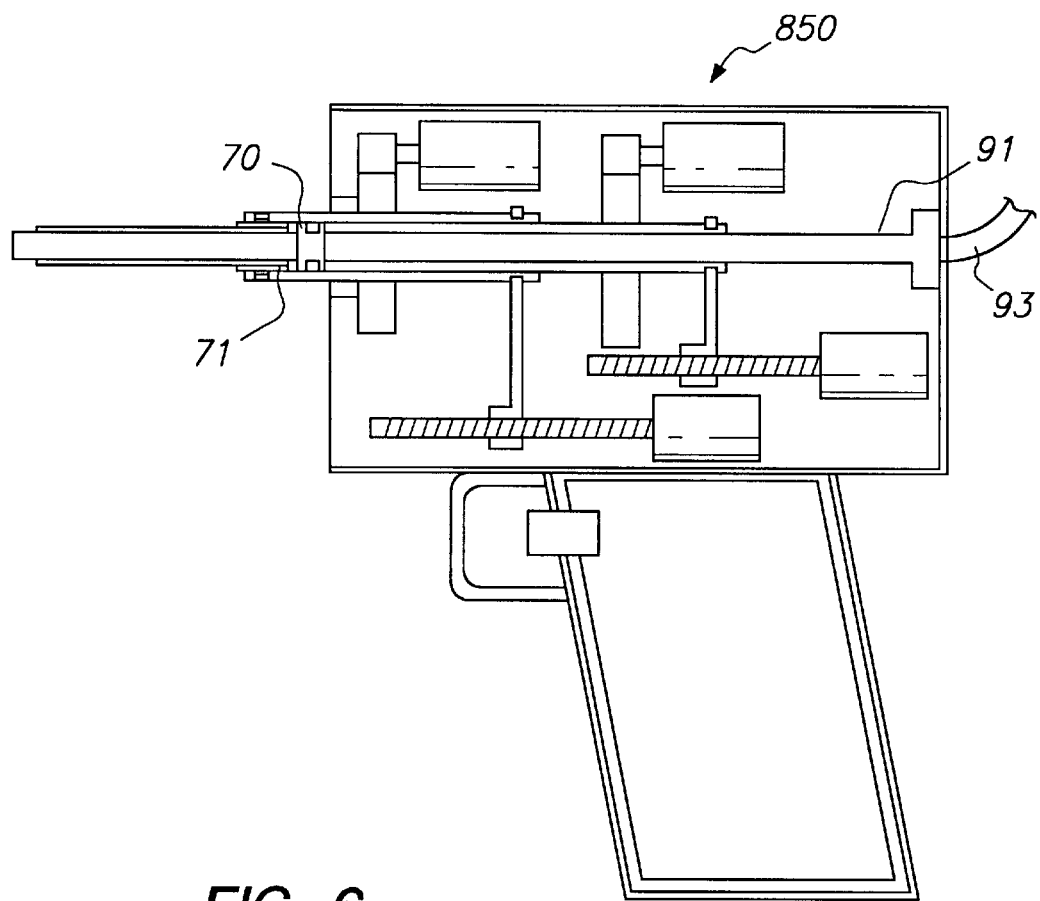
FIG. 6 is a side view of another aspect of a hand piece for performing mechanical TMR and having a single, detachable cutting tip assembly.

In order for the various cutting tip assemblies described above to function as described herein, each cutting tip assembly preferably is linked to a hand held device, such as the hand pieces 85 and 850 shown in FIGS. 5 and 6. Hand pieces 85, 850 allow automatic advancement and rotation of the cutting tip assembly.

Figure 4:
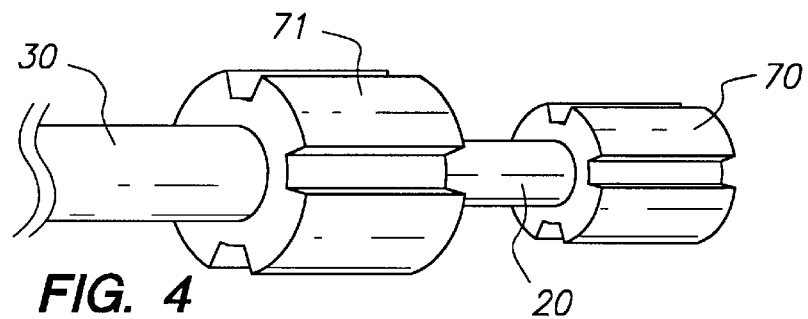
FIG. 4 is a perspective view of a mechanism for mounting a cutting tip assembly of the present invention to a hand piece for rotation and axial movement.

FIG. 4 illustrates an example of linkages 70, 71 which may be used to connect the cutting tip assemblies to the hand pieces. Dual linkages 70, 71 separately mount an inner needle 20 and an outer needle 30 to allow independent rotation and movement of the inner and outer needles. The inside diameter of linkage 71 is larger than the inside diameter of linkage 70 to facilitate loading the linkages into the hand piece and to allow reciprocation of inner needle 20 within outer needle 30. Because inner needle 20 is disposed within outer needle 30, its linkage 71 may be disposed within the linkage 70 for outer needle 30. Preferably, the linkages 70, 71 fit into mating cavities in the hand pieces, although other conventional mounting arrangements may be used. The linkages 70, 71 may snap mount within the mating cavities of the hand pieces to enable new, unused cutting tip assemblies to be quickly and easily connected to the hand pieces. Such drives and their linkages must be capable of providing independent rotational and translation motion for both needles of cutting tip assembly 40. Hence, four separate degrees of freedom, two rotational and two translational, must be provided for cutting tip assemblies having an inner and outer needle. Only one linkage need be provided for the single needle embodiment of FIG. 2. In this FIG. 2 embodiment, the drive and its linkage must be capable of providing independent rotational and translation motion for the tapered needle 402. Hence, two separate degrees of freedom, one rotational and one translational, must be provided for tip 400 of this preferred embodiment.

Referring now to FIGS. 5 and 6 showing the hand pieces 85 and 850, the linkages 70, 71 for the two needle cutting tip assemblies are independently connected to, respectively, reciprocation mechanisms 74, 75 and motor drives 76, 77 to provide both axial movement and rotation. The motor drives 76, 77 may be gear motors operatively connected to a controller (not shown). The controller is activated when the operator pushes actuator 78, such as one or more triggers or buttons, to activate the motor drives 76, 77. The motor drives 76, 77 may be powered by a battery (not shown) and the controller operates to regulate the motor drives to correctly sequence channel creation. Rotating output shafts 79 of the motors 76, 77 engage gear mechanisms 81 which rotate and engage the inner and outer needles 20, 30 and cause rotation thereof.

At the same time as rotation is occurring as described above, lead screws 83 rotate in response to operation of reciprocation mechanisms 74, 75 thereby causing linear movement of piston 91. As piston 91 moves linearly towards linkage 70, inner needle 20 advances in an axial direction because it is operatively connected to reciprocation mechanisms 74, 75 by a bracket 89. Further advancement of the piston 91 causes the outer needle 30 to advance in an axial direction when the piston 91 engages linkage 71. The stroke length of the piston is controlled using mechanical or electrical stops on the lead screws. Alternatively, stepper motors may be used to advance and retract the needles thereby allowing control of the stroke of the piston.

Referring now to FIG. 5, multiple cutting tip assemblies 40 are disposed within a cartridge 80 which is removably mounted to the hand piece 85. The cartridge 80 preferable is generally cylindrical and defines a plurality of apertures for insertion of the cutting tip assemblies 40. FIG. 5 shows the cutting tip assemblies 40 in a linear arrangement for the purpose of illustration only. An advancement mechanism 82 includes a motor drive 84 which, upon activation of the actuator 78, causes rotation of the cartridge 80 to introduce a new cutting tip assembly 40 into aperture 87. As the new cutting tip assembly 40 is rotated into position, the gear motors 76, 77 cause reciprocation and rotation of the cutting tip assembly 40 as described above. Following creation of each channel and movement of the hand piece to a different location on the heart, the trigger is again pressed to reactive the sequence. Any conventional rotational mechanism may be used to rotate the cartridge 80.

FIG. 6 is a hand piece 850 for snap mount attachment of a single cutting tip assembly which may be easily disconnected prior to snap mounting a new tip into place. The FIG. 6 embodiment operates the cutting device in the same manner as described in connection with the FIG. 5 embodiment.

The method of the present invention using a hand piece 85 or 850 with a cutting tip assembly having an inner and outer needle may now be understood. FIG. 1E illustrates that, when activated, piercing tool 42 moves downwardly below the edge of inner needle 20 to create an initial hole through the epicardium prior to retraction upwardly within inner needle 20. FIG. 1A illustrates that, when actuated by trigger 78, inner needle 20 is rotated about its longitudinal axis 28. Lateral axis 28 of inner needle 20 is held substantially perpendicular to the exterior surface 12 of the heart. Movement of the piston 91 causes the inner needle to be translated laterally along longitudinal axis 28 until sharpened edge 26 of inner needle 20 enters the epicardium 12 through the initial hole and travels partway into the myocardium 10. In this way a core 16 of tissue from the myocardium 10 extends into the tubular hollow internal bore 22 of inner needle 20.

FIGS. 1B and 1C illustrate the next step in this method. Inner needle 20 is stabilized in location by ceasing rotation of inner needle 20 and holding inner needle 20 stationary as piston 91 reaches its maximum stroke for inner needle 20. This stabilization may be improved by use of a vacuum applied to tubular hollow internal bore 22 to provide suction upon core 16 to hold it in place during further cutting. As shown in FIG. 6, the piston 91 may be hollow for attachment of a vacuum line 93 communicating with the hollow internal bores of, at least, the inner needle.

Next, outer needle 30 is actuated to rotate about its longitudinal axis 38 and is translated laterally along lateral axis 38, with sharpened edge 36 entering the hole through the epicardium 12 and passing into the myocardium 10 when the piston 91 engages outer needle linkage 71. This translation is continued until outer needle 30 cuts the desired depth of channel into the myocardium 10. In this manner the remainder of the heart tissue to be excised is located within hollow internal bore 32 of outer needle 30. Ideally, this will be a channel that extends completely through the endothelium 14, thus creating a channel extending into the ventricle.

Finally, FIG. 1D illustrates that cutting tip assembly 40, including both inner needle 20 and outer needle 30, is removed from the myocardium 10 after longitudinal withdrawal of both needles, creating a channel 18. Core 16 of heart wall 10 is also removed cleanly if channel 18 extends completely through the endothelium 15.

By providing multiple degrees of freedom of motion to the cutting tip assemblies, the inner needle may be rotated for several turns in a first direction while the advancing outer needle rotates in the opposite direction. Rotation of the inner needle 20 counter clockwise to the direction of rotation of the outer needle 30 compresses the excised tissue and holds it away from the outer needle 30. The excised tissue attached to the inner needle is twisted by the counter rotation thereby reducing its diameter to enhance channel formation and free the excised tissue from the interior wall of outer cutting needle 30. Additionally, counter rotation with the application of counter cutting forces by an applied vacuum is particularly useful to achieve a clean cut through the endothelium without leaving a flap or ragged edge.

The method of the present invention using the FIG. 2 preferred embodiment may now be understood. FIG. 2A illustrates that support means 100, or distal tip of a hand piece 85 or 850, is placed adjacent to the exterior surface 12 of heart wall 10, with internal bore 102 substantially perpendicular to that surface. Tapered needle 402 is disposed within internal bore 102, or within the bore of the hand piece. FIGS. 2B and 2C illustrate the next step in this method. Tapered needle 402 is rotated about its longitudinal axis 408. Then, tapered needle 402 is translated laterally along longitudinal axis 108, with sharpened edge 406 cutting through heart wall 10, creating a core 16 of heart wall 10 contained within internal bore 404 of tapered needle 402.

This translation is continued until tapered needle 402 cuts the desired depth of channel into heart wall 10. In this manner the remainder of the heart tissue to be excised is located within hollow internal bore 404 of tapered needle 402. Ideally, this will be a channel that extends completely through the inner heart wall 14, thus creating a channel extending through heart wall 10.

Figure 2A:
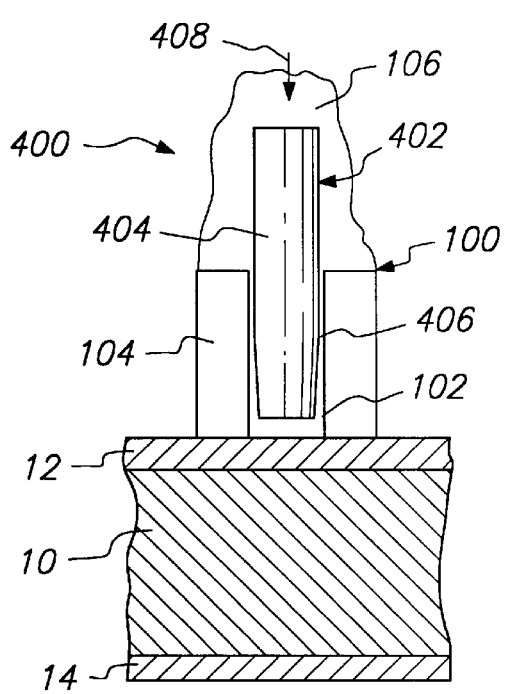
FIGS. 2A–2D illustrate a second preferred method and apparatus according to the present invention, utilizing a cutting tip assembly comprising a single hollow needle within a support means.
Figure 2B:
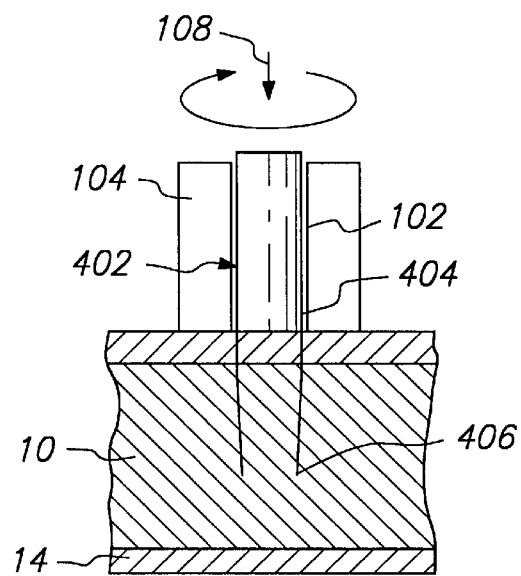
Figure 2C:
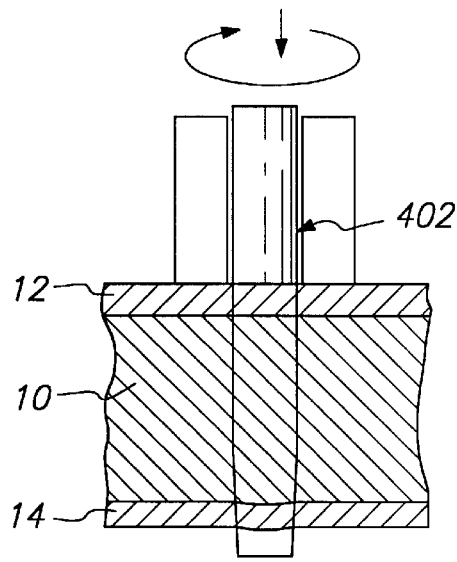
Figure 2D:
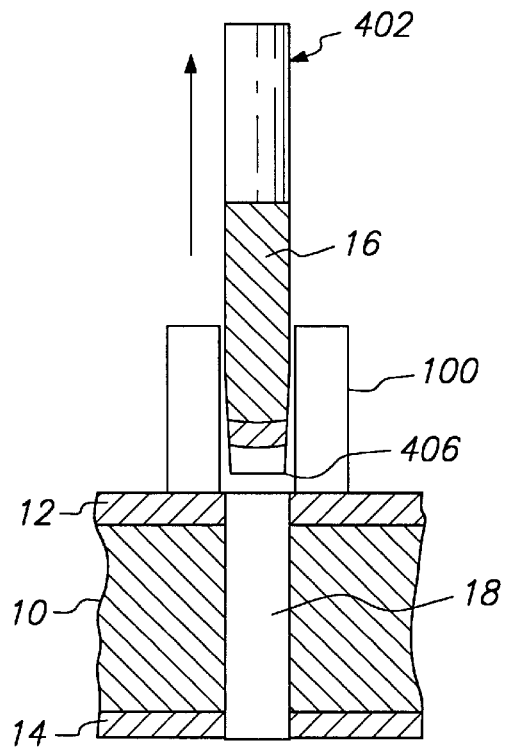

Finally, FIG. 2D illustrates that tapered needle 402 is laterally removed from heart wall 10, creating a channel 18. Core 16 of heart wall 10 is also removed cleanly if channel 18 extends completely through inner heart wall 115, particularly if a vacuum is applied. The tapered configuration of the needle 402 holds the excised tissue and prevents it from exiting through the narrower distal tip when the needle 402 is withdrawn.

Figure 7:
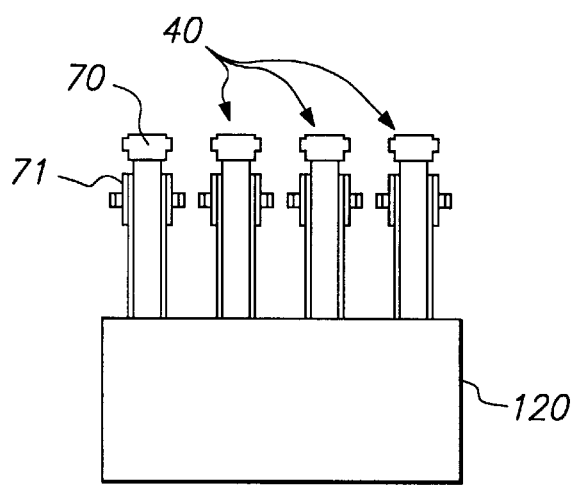
FIG. 7 is a front view of a heating block for cutting tip assemblies.

The creation of viable channels using any of the cutting tip assemblies, with or without the hand pieces discussed above, is greatly facilitated by first heating the cutting tip assemblies to a temperature of at least 60 degrees Celsius. This provides thermal damage to the heart wall 10, in addition to the thermal damage created from frictional engagement of the cutting tip assembly, which has been found to be efficacious in production of viable channels, and simulates the thermal shock of the prior art laser methods. The cartridge embodiment of FIG. 5 may include a separate heating element (not shown), such as a conventional thermal band (not shown) to ensure that each cutting tip assembly is heated as it is rotated into place. Alternatively, a plurality of cartridges 80 may be heated in an oven (not shown) and attached with a snap lock or quick disconnect mechanism to the hand piece. Heated cutting tip assemblies for the FIG. 6 embodiment may be accomplished using a heating block 120 as shown in FIG. 7. The heating block 120 holds a plurality of cutting tip assemblies which snap mount into the hand piece 850. The aperture in the hand piece may be slipped over the linkage at the top of the cutting tip assembly within the heating block and snapped into place without handling the cutting tip assembly.

As will be understood by those familiar with the art, the present invention may be embodied in other specific forms without departing from the spirit or essential characteristics thereof. The scope of the present invention is therefore limited only by the scope of the claims appended hereto.

What is claimed is:

1. A method of forming at least one revascularization channel in a desired portion of a heart wall comprising the steps of:

providing a mechanical cutting assembly having a distal end with an inner needle slidably engaged within a bore of an outer needle defining a cutting edge;

positioning the distal end of the mechanical cutting assembly at a surface of the heart wall;

forming a tissue stabilizing pilot hole through the surface of the heart wall by translating the inner needle into the heart wall;

rotating and translating the outer needle over the inner needle until the outer needle cuts tissue to a desired depth into the wall;

holding and retaining the cut tissue with the inner needle; and retracting the translated inner and outer needles with the retained excised tissue thereby forming at least one revascularization channel.

2. The method of claim 1 further including a step of rotating the inner needle at least during the translation thereof.

3. The method of claim 1 further including a step of rotating the inner needle in a direction counter to a direction of movement of the outer needle.

4. The method of claim 1 further including a step of heating at least one of the inner and outer needles prior to excising tissue.

5. The method of claim 1 further including a step of providing suction to at least a bore of the inner needle at least during cutting of tissue by the outer needle.

6. The method of claim 1 wherein the step of forming a pilot hole is performed by a piercing tip of the inner needle and the step of holding and retaining is performed by an internal bore of the inner needle.

7. The method of claim 1 wherein the step of holding and retaining tissue is performed by a screw-type threaded distal end of the inner needle.

8. The method of claim 1 wherein the step of holding and retaining tissue is performed by an augering drill tipped distal end of the inner needle.

9. The method of claim 1 further comprising the step of cleanly cutting off the distal end of excised tissue by holding the tissue with the inner needle to secure the tissue's position during cutting by the outer needle and by providing a sharp, beveled cutting edge on the outer needle.

* * * * *